US008285021B2

(12) United States Patent
Boese et al.

(10) Patent No.: US 8,285,021 B2
(45) Date of Patent: Oct. 9, 2012

(54) THREE-DIMENSIONAL (3D) RECONSTRUCTION OF THE LEFT ATRIUM AND PULMONARY VEINS

(75) Inventors: Jan Boese, Eckental (DE); Alois Nöttling, Pottenstein (DE)

(73) Assignee: Siemens Aktiengesellschaft, Munich (DE)

( * ) Notice: Subject to any disclaimer, the term of this patent is extended or adjusted under 35 U.S.C. 154(b) by 1159 days.

(21) Appl. No.: 12/113,482

(22) Filed: May 1, 2008

(65) Prior Publication Data
US 2009/0010516 A1  Jan. 8, 2009

Related U.S. Application Data

(60) Provisional application No. 60/916,378, filed on May 7, 2007.

(51) Int. Cl.
*A61B 6/03* (2006.01)
(52) U.S. Cl. ............................ 382/131; 378/4; 600/425
(58) Field of Classification Search ................ 378/4, 68, 378/177, 195; 382/128–134; 600/425
See application file for complete search history.

(56) References Cited

U.S. PATENT DOCUMENTS

| 2005/0054918 | A1 | 3/2005 | Sra | |
| 2006/0120507 | A1* | 6/2006 | Brunner et al. | 378/62 |
| 2008/0051648 | A1* | 2/2008 | Suri et al. | 600/407 |
| 2008/0198972 | A1* | 8/2008 | Rasche | 378/195 |
| 2008/0221435 | A1* | 9/2008 | Rasche | 600/424 |

FOREIGN PATENT DOCUMENTS
WO  WO 2006/028855 A1  3/2006

OTHER PUBLICATIONS

Orlov et al., Three-dimensional rotational angiography of the left atrium and esophagus—A virtual computed tomography scan of the electrophysiology lab?, Published online Oct. 13, 2006, Heart Rhythm, vol. 4, Issue 1, pp. 37-43.*
Sra, Registration of Three Dimensional Left Atrial Images with Interventional systems, 2005, Heart, vol. 91, pp. 1098-1104.*
Haage et al., Reduction of Contrast Material Dose and Artifacts by a Saline Flush Using a Double Power Injector in Helical CT of the Thorax, 2000, American Journal of Roentgenology, vol. 174, pp. 1049-1053.*
Patel et al., Initial Experience with Left Ventricular Lead Placement Using Remote Magnetic Navigation and High Speed Rotational Coronary Sinus Angiography, Mar. 23, 2006, Annual Research Day welcoming Publication for the Annual Research Day Poster presentations held at Caritas St. Elizabeth's Medical Center Seton Auditorium, Poster H3 on p. 22.*
Van de Kraats, 3D Rotational X-Ray guidance for Surgical Interventions, 2005, ISBN 90-393-3859-0, 157 pages.*

(Continued)

*Primary Examiner* — Edward Glick
*Assistant Examiner* — John Corbett
(74) *Attorney, Agent, or Firm* — Lempia Summerfield Katz LLC

(57) ABSTRACT

A method for centering a left atrium and pulmonary veins at an isocenter of an imaging device is provided. The method includes positioning an injection catheter at a bifurcation of a pulmonary artery; obtaining an anterior or posterior flouroscopic image of area including and/or surrounding the left atrium and pulmonary veins; and moving the imaging device, patient support, or the combination thereof, such that the injection catheter and a spine of a patient are displayed in the fluoroscopic image.

20 Claims, 1 Drawing Sheet

OTHER PUBLICATIONS

Chen et al., Improved determination of biplane imaging geometry from two projection images and its application to three-dimensional reconstruction of the coronary arterial trees, 1997, Medical Physics, vol. 24, No. 5, pp. 633-654.*

Kurp, Axiom Artis FD Systems, DynaCT—A breakthrough in Interventional 3D Imaging, Jan. 2005, Reprint from Medical Solutions, Siemens Medical, pp. 46-51.*

Lauritsch et al., Toward Cardiac Angiographic Computed Tomography, 2005 IEEE Nuclear Science Symposium Record, vol. 4, pp. 2350-2354.*

De Buck et al., An Augmented Reality System for Patient-Specific Guidance of Cardiac Catheter Ablation Procedures, 2005, IEEE Transactions on Medical Imaging, vol. 24, No. 11, pp. 1512-1524.*

Thiagalingam et al., Intraprocedural Volume Imaging on the Left Atrium and Pulmonary Veins with rotational X-ray Angiography, Published online Nov. 14, 2007, original manuscript, Journal of Cardiovascular Electrophysiology, vol. 19, No. 3, pp. 293-300.*

Manzke et al., Intra-operative Volume Imaging of the Left Atrium and Pulmonary Veins with Rotational X-Ray Angiography, Oct. 2, 2006, MICCAI 2006, Poster session P1-4, Poster M58, LNCS 4190, pp. 604-611.*

Manzke et al., Rotational X-ray angiography: a method for intra-operative volume imaging of the left-atrium and pulmonary veins for atrial fibrillation ablation guidance, Feb. 18, 2007, Medical Imaging 2007: Visualization and Image-Guided Procedures, SPIE vol. 6509, pp. 0T-1 to 0T-9.*

Chinese Office Action dated Jan. 27, 2011 for corresponding Chinese Patent Applicaton No. 200810109266.4 with English translation.

"Heart Rhythm 2007", AFib Summit, Denver, Colorado, May 9-12, 2007, Abstract Information, 2 pages.

Manzke et al., "Intra-Operative Volume Imaging of the Left Atrium and Pulmonary Veins with Rotational X-Ray Angiography," Philips Research North America, Clinical Sites Research, Briarcliff Manor, New York, MICCAI 2006, LNC 4190, 2006 pp. 604-611 (7 pages).

Oral, Hakan, M.D., Editorial Commentary from the Division of Cardiovascular Medicine, University of Michigan, Ann Arbor, Michigan, "Rotational Angiography: A Novel Application of an Old Concept," 2007 Heart Rhythm Society, Heart Rhythm, vol. 4, Issue 1, Jan. 2007, pp. 44-45 (2 pages), Available online Nov. 10, 2006.

Orlov et al., "Three-Dimensional Rotational Angiography of the Left Atrium and Esophagus—A Virtual Computed Tomography Scan in the Electrophysiology Lab?", *Heart Rhythm*, vol. 4., No. 1, Jan. 2007, pp. 37-43 (7 pages), Available online Oct. 13, 2006.

* cited by examiner

THREE-DIMENSIONAL (3D) RECONSTRUCTION OF THE LEFT ATRIUM AND PULMONARY VEINS

This patent document claims the benefit of U.S. Provisional Patent Application No. 60/916,378, filed May 7, 2007, which is hereby incorporated by reference.

BACKGROUND

The present embodiments relate to three-dimensional (3D) reconstruction of the left atrium and pulmonary veins.

Computer tomography (CT) and magnetic resonance imaging (MRI) may be used to obtain images of the human body, such as the left atrium and pulmonary veins. The left atrium is one of the four chambers in the human heart. The left atrium receives oxygenated blood from the pulmonary veins and pumps the blood into the left ventricle. The four pulmonary veins carry oxygen-rich blood from the lungs to the left atrium of the heart. The lungs receive blood from the pulmonary artery.

Computer tomography (CT) and magnetic resonance imaging (MRI) are used to produce images of the left atrium and pulmonary veins. The images may be used to determine the morphology of the left atrium and the number, size and position of the pulmonary veins. This anatomical information is desired, because ablation in the left atrium is mainly performed around the ostia openings of the pulmonary veins.

Several days may pass between the taking of the images and the therapy. During this time, anatomical structures are often displaced. Moreover, the shape and size of the atrium may change during this time.

Two different 3D data sets may be obtained using an X-ray system that is employed for the therapy. The imaging of the 3D data may be performed immediately (directly) prior to or in the course of the therapy. Two different data sets of the left atrium are obtained. The first data set is of one half of the left atrium and pulmonary veins, and the second data set is of the other half of the left atrium and pulmonary veins. The first and second data sets are used to obtain two different 3D representations of the left atrium and pulmonary veins. Obtaining the data sets requires injecting a contrast agent into the patient and applying a radiation dosage for each the first and second data sets. In other words, a contrast agent is injected into the patient twice and the patient is subject to a radiation dosage twice. The two 3D representations are fused together to obtain a single 3D representation of the left atrium and pulmonary veins.

Obtaining the first and second data sets is required because X-ray systems, which are used in electrophysiology and cardiology, are equipped with a small (e.g., 20 cm×20 cm) detector. Because of the size of the detector, it is difficult to obtain a single data set representing the left atrium and pulmonary veins. The size of the detector makes it difficult to position the detector, such that the detector obtains a data set that may be used to generate a 3D representation of the left atrium and all of the pulmonary veins.

SUMMARY AND DESCRIPTION

The present embodiments relate to three-dimensional (3D) reconstruction of the left atrium and pulmonary veins. The reconstructed data set may be used in the course of therapy (e.g., ablation) in electrophysiology.

The present embodiments may obviate one or more of the drawbacks or limitations inherent in the related art. For example, in one embodiment, a 3D representation of the left atrium and pulmonary veins uses one contrast agent injection and one 3D data set acquisition. The method reduces the contrast medium injected into and X-ray dosage applied to the patient.

A method for generating a 3D representation of the left atrium and the pulmonary veins ostia opening into the left atrium is provided. An X-ray detector (e.g., 20 cm×20 cm) may be used to obtain (acquire) a 3D-data set, which can be used to generate a 3D representation of the left atrium and the pulmonary veins. The 3D representation may be used in the therapy. The method may be used with any size detectors, such as small cardiology detector or a larger detector.

In one embodiment, the method includes positioning of the left atrium in the isocenter of the C-arch with fluoroscopic control (capability) on the basis of anatomical structures (spine) and an already introduced (positioned) injection catheter. The catheter may be used to inject a contrast agent (medium) into the pulmonary veins. Positioning takes place in the recording geometry, for example, source-image distance (SID), in which the 3D-image acquisition is subsequently performed.

An anatomic structure and the catheter may be used to position the left atrium and pulmonary veins at the isocenter of the imaging device. The volume of interest, which can be detected by the detector, is only approximately 12 cm. An area representing the left atrium and the pulmonary veins is approximately 10 to 11 cm.

Examination and measurements of numerous split images of the patient have shown that the distances between the spine and the center of the left atrium are almost identical, regardless of the size and girth of the patient. A centering protocol includes positioning anatomical structures (e.g., spine, and the already inserted catheter) at the isocenter of the imaging device. Since the anatomical structures are visible in the fluoroscopic image, the left atrium may be positioned without using a contrast agent.

The time difference between the contrast agent injection into the pulmonary artery and the contrast agent accumulation in the left atrium may be determined with digital subtraction angiography (DSA) or digital radiography (DR). The delay time from injection to x-ray is calculated from this delay time. The DSA image may also be used for positioning of the left atrium. Using the delay time, 3D-image acquisition (e.g., with a rotational angiography device) may include automatic contrast agent injection and set X-ray delay.

A test bolus may be used with digital subtraction angiography (DSA) to determine the x-ray delay time. Since the injection of the contrast agent takes place into the main stem of the pulmonary artery, or into the bifurcation of the left and right pulmonary arteries, the contrast agent takes a path via the lungs and, with a delay of several seconds, finally arrives in the left atrium via the pulmonary veins. 3D-image acquisition is to be started at this point in time.

Since this delay time is different from one patient to the other (approximately 5 to 10 s), and the length of injection (e.g., the amount of contrast agent injected) the delay time is determined with a short test injection (test bolus) and a simultaneous DSA or DR series, The DSA or DR images taken within the recording geometry of the subsequent 3D-image acquisition may be used for the exact fine positioning of the patient.

The catheter may be rinsed (flushed) immediately at the termination of the contrast agent injection. The rinsing (flushing) may be manual or automatic. A catheter having a contrast agent still disposed within may cause artifacts in the reconstructed volume data set.

The injection catheter is rinsed before the 3D data set is acquired. The contrast agent in the injection catheter may cause strong artifacts in the reconstructed split images and in the 3D-data set. The catheter may be rinsed at the end of the contrast medium injection, for example, with a saline solution. This rinsing of the catheter may take place manually and/or automatically, with a double-piston injector.

A 3D data set is acquired. The 3D data set is reconstructed from two-dimensional images acquired from different directions.

A 3D representation of the left atrium and the pulmonary veins may be generated with the use of algorithms for soft tissue reconstruction. The algorithms may include truncation correction, scatter radiation correction, and excessive radiation correction.

Following the 3D-reconstruction, the left atrium, including the pulmonary veins, may be segmented out of the 3D-data set. The image segmentation of the left atrium and pulmonary veins may be automatic or manual. This can take place either by hand (e.g., with the aid of clip planes and punching), or automatically with the use of a segmentation tool (e.g., InspaceEP). Image segmentation may include identifying parts of the image and distinguishing those parts from other parts of the image.

The volume data (3D data set) may be integrated into the therapy system. The 3D data of the left atrium and the pulmonary veins may be integrated into a therapy or examination system. The volume data set may be imported into the therapy system for navigation and ablation. The segmented data may be directly imported, or the therapy system may be used for segmentation. Geometric information from the X-ray system can be used for mapping the 3D-data of the therapy system. The therapy (ablation) can be directly performed with the aid of this morphologic information. Geometrically correct blending-in, or superposition, of the 3D-data during fluoroscopic examination.

DETAILED DESCRIPTION

Figure 1:
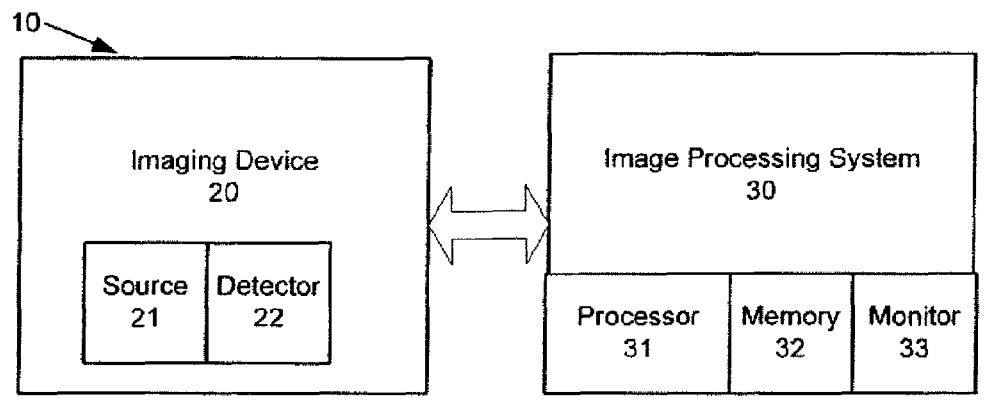
FIG. 1 illustrates one embodiment of an imaging system.

FIG. 1 shows an imaging system 10 for generating a three-dimensional (3D) representation. The imaging system 10 may include an imaging device 20 and an image processing system 30. Additional, different, or fewer components may be provided.

The imaging system 10 is a medical workstation, an x-ray system, a biplane system, a computed tomography (CT) system, an angiography system, a magnetic resonance system, a fluoroscopy system, a C-arm system, a nuclear medicine system, a positron emission tomography (PET) system, a pre-clinical imaging system, a radiography system, a radiation oncology system, or other now known or latter developed imaging system. The imaging system 10 generates a dataset representing a region of the patient, and may generate an image or representation of the region using the dataset.

The imaging system 10 may be used to plan and monitor a medical process, such as an ablation, heart surgery, or other medical operation. The imaging system 10 may obtain data and generate images using the data. The imaging system 10 provides automated assistance to a physician for planning and monitoring a medical intervention. For planning, the imaging system 10 may generate a three-dimensional (3D) representation of the medical intervention region prior to the medical process and plan and/or prepare for the medical process using the 3D representation. For example, the imaging system 10 may be used to obtain a 3D data set of the left atrium and pulmonary veins and generate a 3D representation of the left atrium and pulmonary veins.

The imaging device 20 may include an imaging source 21 and an imaging detector 22. Additional, different, or fewer components may be provided. For example, the imaging device 20 may include two or more sources and/or two or more detectors, such as in biplane device.

The imaging device 20 may be a computed tomography (CT) device, a biplane device, a magnetic resonance device, an angiography device, a fluoroscopy device, a C-arm based X-ray system, other now known or later developed imaging devices, or any combination thereof. For example, the imaging device 20 may be a biplane device. The biplane device may operate as a CT device, such as a DynaCT device, to obtain a set of data representing a 2D region; for example, by rotation of a source and detector around the area to be imaged. The set of data representing a 2D region may be used to obtain a 3D data set and generate a 3D representation. The biplane device may also operate as a biplane fluoroscopy device with two detectors and two sources. The biplane fluoroscopy device may obtain data from at least two different angles at the same point in time. The data may be used to generate a 2D shadow projection. The projection may be a fluoroscopic projection.

The imaging source 21 and imaging detector 22 may be disposed opposite each other. For example, the imaging source 21 and imaging detector 22 may be disposed on diametrically opposite ends of a C-arm. In another example, the source 21 and detector 22 are connected inside a gantry. The region to be imaged (imaging region) is located between the source 21 and detector 22. The amount, shape, and/or angle of radiation may be adjusted to scan the region. All, a portion, or none of a patient may be disposed in the imaging region. For example, the medical intervention area in the patient, such as a human organ or a body part, may be disposed in the imaging region for generation of images of the intervention point.

In one embodiment, the imaging device 20 may include two or more sources and/or two or more detectors. For example, the imaging device 20 may be a biplane device having a first and a second C-arm, each C-arm has a source and detector disposed on diametrically opposite ends of the C-arms. The first and second C-arms may be moved relative to each other to obtain image data of the imaging region from two different directions at the same point in time.

The imaging source 21 may be a radiation source, such as an x-ray source. The imaging source 21 may emit radiation to the detector 22. The imaging detector 22 may be a radiation detector, such as a digital x-ray detector. The imaging detector 22 may detect the radiation emitted from the imaging source 21. Image data is generated based on the amount or strength of radiation detected. For example, the imaging detector 22 detects the strength of the radiation received at the imaging detector 22 and generates image data based on the strength of the radiation.

The detector 22 detects data representing a two-dimensional (2D) region. The data represents a 2D imaging region from one direction. The data representing the 2D region may be used to generate a 2D image or combined with data from different directions to generate a three-dimensional (3D) representation. For example, a biplane system may be used to obtain data representing 2D regions from two different directions at the same time. The data may be used to generate a 2D shadow projection of the imaging region.

The imaging device 20 may be communicatively coupled to the image processing system 30. The imaging device 20 may be connected to the image processing system 30 by a communication line, cable, wireless device, communication circuit, or other communication device. For example, the imaging device 20 may communicate image data to the image processing system 30. In another example, the image processing system 30 may communicate an instruction, such as a position or angulation instruction, to the imaging device 20. All, some, or none of the image processing system 30 may be disposed in the imaging device 30. For example, the image processing system 30 may be disposed in the same or a different room as the imaging device 30, or in the same or different facilities.

The image processing system 30 may include a processor 31, memory 32, and monitor 33. Additional, different, or fewer components may be provided. For example, the image processing system 30 may include an input device, such as a keyboard, mouse, compact disc drive or other now known or later developed input device.

The processor 31 is a general processor, digital signal processor, application specific integrated circuit, field programmable gate array, analog circuit, digital circuit, combinations thereof, or other now known or later developed processor. The processor 31 may be a single device or a combination of devices, such as associated with a network or distributed processing. Any of various processing strategies may be used, such as multi-processing, multi-tasking, parallel processing, or the like. The processor 31 is responsive to instructions stored as part of software, hardware, integrated circuits, firmware, micro-code or the like.

The processor 31 may generate an image, image representation, or image projection using the image data. The processor 31 processes image data received from the imaging device 20 and generates one or more fluoroscopic images, top-view images, in-plane images, orthogonal images, side-view images, 2D images, 3D representations, 2D projections, progression images, multi-planar reconstruction images, other now known or later developed images, or the combination thereof from the image data. For example, the processor 31 may generate a 3D representation from the image data obtained prior to the medical intervention and a 2D projection image from the image data obtained during the medical intervention.

The processor 31 may generate at least two 2D images from at least two different directions. The 2D images may represent the area to be imaged during a medical procedure, such as the recording geometry. For example, the at least two 2D images may be obtained from a bi-plane system used to monitor the medical procedure.

The processor 31 may generate a 3D representation from a 3D image data set. The 3D data set may include data representing 2D planes from a plurality of different directions. The processor 31 combines the 2D data from a plurality of different directions to acquire the 3D representation.

The processor 31 may position the imaging device 20 to be positioned, such that the left atrium and pulmonary veins are positioned at the isocenter of the imaging device. The imaging device 20 may be positioned at an anterior/posterior position (e.g., with a c-arm device). The processor 31 may cause the imaging device and/or patient support to be moved in combination such that the left atrium and pulmonary veins are positioned at the isocentric position. As displayed on the monitor 33, the vertebrae (spine) may be positioned at the center of the monitor 33 and the catheter (pig tail) at the top of the image displayed on the monitor 33. The vertebrae may be displayed slightly left or right (e.g., 1.5 cm) of the center on the image being displayed on the monitor 33.

The processor 31 may calculate an x-ray delay time. The processor 31 may determine the time it takes for a test bolus of the contrast agent to pass from the injection catheter to the left atrium. The processor may use digital subtraction angiography (DSA) or digital radiography (DR) to determine the time between the contrast agent injection into the pulmonary artery and the contrast agent accumulation in the left atrium. The DSA or DR image may be used for positioning of the left atrium.

The processor 31 may initiate an injection of a contrast agent. The processor 31 may receive a command from an input device or automatically initiate the injection. For example, a physician may provide a command to being the injection of the contrast agent. The processor 31 may determine the time that the injection of the contrast agent occurred.

The processor 31 may initiate (cause) rinsing of the injection catheter. The processor 31 may detect the injection of the contrast agent and initiate the rinsing of the injection catheter. The injection catheter may be rinsed before the 3D data set is acquired.

The processor 31 may initiate a 3D data set to be acquired. Using the delay time, 3D-image acquisition (e.g., with a Dyna DR series) may include automatic contrast agent injection and set X-ray delay. For example, the processor 31 may use the time that the injection of the contrast agent occurred and the x-ray delay time to determine when the 3D data set should be acquired.

The processor 31 may use algorithms to generate a 3D representation of the left atrium and pulmonary veins. Any now known or later developed algorithm may be used for constructing a 3D representation. For example, algorithms for the reconstruction of soft tissue may be used to construct the 3D representation. The algorithms may be used for truncation correction, scatter radiation correction, and excessive radiation correction.

The processor 31 may segment the left atrium and pulmonary veins out of the 3D data set. The processor 31 may change the 3D data set, such that the segmented regions are different from the other regions. Adjacent regions are significantly different with respect to the same characteristic(s). For example, the left atrium and pulmonary veins may be darker than other areas surrounding the left atrium, such as the lung. The other areas surrounding the left atrium and pulmonary veins may be "ghost" images. Image segmentation may be automatic or manual.

The processor 31 may integrate (blend) the 3D data set into an x-ray image. The processor 31 may communicate the 3D data set to a therapy system or integrate the 3D data set into the therapy process performed with the imaging device 20. The geometric information (e.g., tomography) of the left atrium and pulmonary veins may be used to map the 3D representation according to the therapy system or imaging device 20. For example, the 3D representation may be registered with an x-ray image of the examination process. The x-ray image obtained during examination may be superimposed geometrically onto the 3D data set or 3D representation.

The processor 31 may communicate with the memory 32. The processor 31 and memory 32 may be connected by a cable, circuit, wireless-connection, or other communication coupling. Images, data, and other information may be communicated from the processor 31 to the memory 32 or vice-versa. For example, the processor 31 may communicate the generated images, image data, or other information to the memory 32. The processor 31 may retrieve information, images, image data, or other data from the memory 32.

The memory 32 is a computer readable storage media. The computer readable storage media may include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 32 may be a single device or a combination of devices. The memory 32 may be adjacent to, part of, networked with and/or remote from the processor 31.

The memory 32 may be a computer readable storage media having stored therein data representing instructions executable by the programmed processor 31 for monitoring a medical intervention. The memory 32 stores instructions for the processor 31. The processor 31 is programmed with and executes the instructions. The functions, acts, methods or tasks illustrated in the figures or described herein are performed by the programmed processor 31 executing the instructions stored in the memory 32. For example, the instructions may include acts 220, 240, and 250. The functions, acts, methods or tasks are independent of the particular type of instructions set, storage media, processor or processing strategy and may be performed by software, hardware, integrated circuits, firm ware, micro-code and the like, operating alone or in combination. The instructions are for implementing the processes, techniques, methods, or acts described herein.

In one embodiment, a computer readable storage media stores data representing instructions executable by a programmed processor for monitoring a medical intervention. The instructions may include obtaining a 3D data set and generating a 3D representation.

The monitor 33 is a CRT, monitor, flat panel, a general display, LCD, projector, printer or other now known or later developed display device for outputting determined information. The monitor 33 may display images, representation, or information. For example, the monitor 33 may display a 3D representation of the left atrium and pulmonary veins. The 3D representation may be a segmentation of the left atrium and pulmonary veins. In another example, the monitor 33 may display images of a therapy or surgery area during the medical process. The images may be obtained using another imaging device and transmitted to the imaging system 10 for display on the monitor 33.

The monitor 33 may display an image of the spine and the injection catheter. For example, the imaging device may be used to obtain an image of the left atrium and pulmonary veins, such that the spine and injection catheter are displayed on the monitor 33 at the same time.

Figure 2:
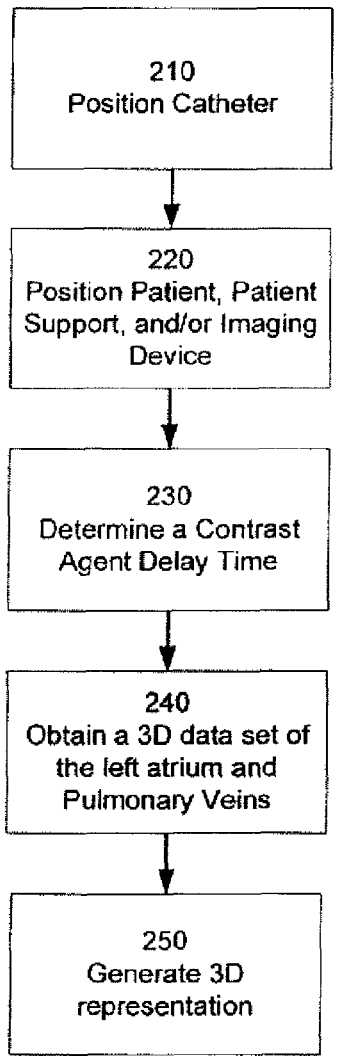
FIG. 2 illustrates one embodiment of a method for generating an three-dimensional representation of the left atrium and pulmonary veins.

FIG. 2 shows a method for generating a 3D representation of the left atrium and pulmonary veins. The method is implemented using the system 10 of FIG. 1 or a different system. The acts may be performed in the order shown or a different order.

The method may include positioning a catheter [act 210]; positioning an imaging device [act 220]; determining a contrast medium delay time [act 230]; obtaining a 3D data set of the left atrium and pulmonary veins [act 240]; and generating a 3D representation of the left atrium and pulmonary veins [act 250]. Additional, different, or fewer acts than shown in FIG. 2 may be provided. For example, the method may include registering a 3D representation of the left atrium and pulmonary veins obtained before the medical process with a representation of the left atrium and pulmonary veins obtained during the medical process.

In act 210, a catheter is positioned for use during a medical process. A catheter may be inserted into a body cavity, duct or vessel. Catheters may be used to provide drainage, injection of fluids, and/or access by surgical instruments. For example, during heart surgery, an injection catheter (e.g., pig tail) may be disposed in the bifurcation of the pulmonary artery. An injector may be connected to the catheter to inject a contrast agent into the pulmonary artery. From the pulmonary artery, the contrast agent is drawn into the lung and subsequently into the pulmonary veins, which connect to the left atrium of the heart.

An imaging system may used to assist with act 210. For example, an imaging system may provide images of the catheter relative to the bifurcation of the pulmonary artery, so that a physician can manually position the catheter in a desired position.

Act 220 may include positioning a patient support, a patient, and/or an imaging device. Additional, different, or fewer positioning acts may be provided. The patient support, patient, and/or imaging device may be positioned such that the left atrium and pulmonary veins are disposed at the isocenter of an imaging device used to obtain the 3D data set.

The patient support (stand) may be positioned. The patient support may be moved up or down or may be moved in a longitudinal or transverse direction. The patient support may be moved to a surgery, therapy, or examination position. For example, a physician may prefer having a patient at a defined height during a surgery. The patient support may adjust to position the patient at the defined height or tilt. The patient support may be positioned in combination with the positioning of the imaging device (discussed below). For example, the patient support may be moved to compensate for restrictions of imaging device movement.

The patient may be positioned on the patient support. The patient may be positioned on his side, back, or stomach. The patient may be positioned based on the surgery, therapy, or examination process to be performed. For example, the patient may be positioned on his back during heart surgery.

The imaging device may be positioned to a defined surgery, therapy, or examination imaging device position. For example, the imaging device may be moved (e.g., in combination with the patient support) to a desired position. The imaging device may be used to view a portion of the area that will be imaged during the acquisition of the 3D data set (e.g., recording geometry). For example, the imaging device may acquire a 2D image of the left atrium and the pulmonary veins.

The imaging device may be moved manually, automatically, or a combination thereof. To obtain a 3D data set of the left atrium and the pulmonary veins, the imaging device should be moved to an anterior/posterior (A/P) position. For example, a C-arm imaging device may be disposed with the radiation source facing (and closest to) the chest of a patient, while the detector is facing (and closest to) the back of the patient.

The left atrium and pulmonary veins may be isocentrically positioned using anatomic structures. The imaging device and/or patient support may be moved to bring the left atrium and pulmonary veins to an isocentric position. For example, using a monitor to illustrate the imaging device view, the imaging device or patient support may be moved to center the vertebrae on the monitor and the catheter (pig tail) at the top of the image. The vertebrae should be displayed slightly left (or right) (e.g., 1.5 cm) of the center of the display.

In act 230, an x-ray delay time is determined. Act 230 may include using a test bolus and digital subtraction angiography (DSA) or digital radiography (DR) to determine the x-ray delay time. Additional, different, or fewer acts may be provided.

As discussed below, prior to the acquisition of the 3D data set, a contrast agent is injected into the patient through the injection catheter. Since the contrast agent is injected into the main stem of the pulmonary artery, or into the bifurcation of the left and right pulmonary arteries, the contrast agent passes through the lungs and pulmonary veins before arriving in the left atrium. Since the 3D data set is acquired once the contrast agent reaches the left atrium, the time from injection of the contrast agent until the time that the contrast agent reaches the left atrium is the x-ray delay time. The x-ray delay time may vary depending on the patient. The x-ray delay time may be approximately 5 to 10 seconds.

The x-ray delay time may be determined by injecting a test bolus into the injection catheter and using a digital subtraction angiography (DSA) or digital radiography (DR) series. DSA is a type of acquisition technique used to visualize blood vessels in a bony or dense soft tissue environment. Images are produced using a contrast agent by subtracting a pre-contrast bolus image or the mask from later images, once the contrast agent has been introduced into a structure. The test bolus may be all, some, or none of the contrast agent injection used prior to the 3D data set acquisition. For example, the amount of contrast agent injected for the test bolus catheter may be less than the amount injected just prior to the acquisition of the 3D data set. Using the DSA images, the x-ray delay time may be determined. The x-ray delay time may be determined automatically or manually.

In act 240, a 3D data set of the left atrium and pulmonary veins is acquired. Act 240 may include inputting variables, injecting contrast agent, rinsing the injection catheter, and acquiring a 3D data set of the left atrium and pulmonary veins. Additional, different, or fewer acts may be provided. For example, variables may not be input.

Variables may be input into an imaging system. Any variable impacting the acquisition of the 3D data set may be input into the imaging system. For example, x-ray delay time may be used as a variable. The x-ray delay time may be automatically determined by the imaging system or input into the imaging system from a remote system or manually.

A contrast agent may be injected into the patient's body using the injection catheter. For example, a contrast agent may be injected into the patient's body from an injection catheter positioned at the bifurcation of the pulmonary artery.

The injection catheter may be rinsed. Rinsing the injection catheter may include removing contrast agent from inside the catheter. After the contrast agent is injected into the patient's body, but before the 3D data set is acquired, the injection catheter may be rinsed. A saline solution may be used to rinse the injection catheter. The rinsing may be automatic or manual. For example, a double-piston injector may be used to automatically rinse the injection catheter.

A 3D data set of the left atrium and pulmonary veins may be acquired. The 3D data set may include two or more two-dimensional (2D) images from different directions. An imaging device may be used to obtain the 3D data set. For example, acquisition of the 3D data set may include rotational imaging. The imaging device may obtain fluoroscopic images during a positioning process and x-ray images from two or more directions during an acquisition of a 3D data set process.

In act 250, a 3D representation of the left atrium and pulmonary veins is generated. Act 250 may include reconstructing a 3D representation of the left atrium and pulmonary veins and segmentation of the 3D representation.

A 3D representation of the left atrium and pulmonary veins may be constructed from the 3D data set. Any now known or later developed algorithm may be used for constructing a 3D representation. For example, algorithms for the reconstruction of soft tissue may be used to construct the 3D representation. The algorithms may be used for truncation correction, scatter radiation correction, and excessive radiation correction.

The left atrium and pulmonary veins may be segmented from the 3D representation. Image segmentation may include partitioning a digital image into multiple regions (sets of voxels). The image segmentation simplifies or changes the representation of an image into something that is more meaningful and easier to analyze. Image segmentation is typically used to locate objects and boundaries (lines, curves, etc.) in images. Image segmentation provides a set of regions that collectively cover the entire image, or a set of contours extracted from the image (e.g., edge detection). Each of the pixels in a region are similar with respect to some characteristic or computed property, such as color, intensity, or texture. Adjacent regions are significantly different with respect to the same characteristic(s). For example, the left atrium and pulmonary veins may be darker than other areas surrounding the left atrium, such as the lung. The other areas surrounding the left atrium and pulmonary veins may be "ghost" images. Image segmentation may be automatic or manual.

The 3D representation, reconstruction, or data set may be integrated into an electrophysicological mapping system. The therapy system may use the geometric information (e.g., tomography) of the left atrium and pulmonary veins to map the 3D representation according to the therapy system. For example, the segmented data set or the 3D data set may be imported into the therapy system.

The 3D representation or 3D data set may be blended with an x-ray image obtained during an examination or therapy procedure. For example, the 3D representation may be registered with an x-ray image of the examination process. The x-ray image obtained during examination may be superimposed geometrically onto the 3D data set or 3D representation or vice versa.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A method for generating a three-dimensional (3D) representation of a left atrium and pulmonary veins, the method comprising:
    positioning the left atrium at an isocenter of an imaging device as a function of an injection catheter and a spine of a patient;
    obtaining a 3D-data set of the left atrium and pulmonary veins using the imaging device with the left atrium positioned at the isocenter; and
    generating a 3D representation of the left atrium and pulmonary veins using the 3D-data set.

2. The method as claimed in claim 1, wherein positioning the left atrium at the isocenter of the imaging device includes positioning the injection catheter and the spine of the patient in a recording geometry for obtaining the 3D data set, wherein fluoroscopy is used to illustrate a recording geometry.

3. The method as claimed in claim 1, further comprising:
determining an X-ray delay time using a test bolus and digital subtraction angiography (DSA) imaging.

4. The method as claimed in claim 1, further comprising:
rinsing the injection catheter after injection of a contrast medium and before obtaining the 3D-data set.

5. The method as claimed in claim 1, wherein generating comprises reconstructing soft tissue using algorithms.

6. The method as claimed in claim 1, further comprising:
segmenting the left atrium and the pulmonary veins in the 3D data set.

7. The method as claimed in claim 1, wherein the 3D representation is integrated into a electrophysicological mapping system.

8. The method as claimed in claim 1, further comprising:
overlaying the 3D representation with an examination image of the left atrium and the pulmonary veins.

9. The method as claimed in claim 1, further comprising:
positioning the injection catheter at a bifurcation of a pulmonary artery, and injecting a single contrast medium into the pulmonary artery.

10. The method as claimed in claim 1, further comprising displaying a view from the imaging device, and wherein positioning comprises positioning the injection catheter at a top of the displayed view and positioning the spine of the patient near a center of the displayed view.

11. A system for generating a three-dimensional (3D) representation of the left atrium and pulmonary veins, the system comprising:
an imaging device operable to obtain an image of the left atrium and the pulmonary veins as a function of an injection catheter and a spine of a patient; and
an image processing device having a monitor that is operable to display the image of the left atrium and the pulmonary veins,
wherein the imaging device is operable to be positioned such that the monitor displays the spine of a patient and the injection catheter at a same time.

12. The system as claimed in claim 11, wherein the imaging device is positioned in an anterior or posterior position.

13. The system as claimed in claim 11, wherein the injection catheter is disposed at a bifurcation of a pulmonary artery.

14. The system as claimed in claim 11, wherein the imaging device is operable to obtain a fluoroscopic image and a 3D data set of the left atrium and the pulmonary veins.

15. The system as claimed in claim 14, wherein the 3D data set includes two or more two-dimensional (2D) images of the left atrium and the pulmonary veins from different directions.

16. The system as claimed in claim 15, wherein the image processing device is operable to generate a 3D representation of the left atrium and the pulmonary veins as a function of the 3D data set.

17. The system as claimed in 16, wherein the image processing device is operable to segment the left atrium and the pulmonary veins from the 3D representation.

18. An imaging system comprising:
an image processing device operable to position a left atrium and pulmonary veins as a function of an injection catheter and a spine of a patient and further operable to instruct an imaging device to obtain an anterior or posterior fluoroscopic image of an area including, surrounding, or including and surrounding the left atrium and the pulmonary veins,
wherein the image processing device is operable to move the imaging device, a patient support, or a combination thereof, such that the injection catheter and the spine of the patient are displayed in the fluoroscopic image.

19. The imaging system as claimed in claim 18, wherein the image processing device is operable to rotate the imaging device around the patient to obtain two-dimensional (2D) images of the left atrium and the pulmonary veins from different directions.

20. The imaging system as claimed in claim 19, wherein the image processing device is operable to generate a 3D representation of the left atrium and the pulmonary veins from the two-dimensional (2D) images.

* * * * *